United States Patent [19]

Larsson

[11] Patent Number: 4,505,935
[45] Date of Patent: Mar. 19, 1985

[54] PROTECTIVE LAYER ON SKIN, MUCOUS MEMBRANE OR OTHER BODY TISSUE

[76] Inventor: Viktor K. Larsson, Kämpagränd 5C, S 223 76 Lund, Sweden

[21] Appl. No.: 409,972

[22] Filed: Aug. 20, 1982

Related U.S. Application Data

[63] Continuation of Ser. No. 147,741, May 8, 1980, abandoned.

[30] Foreign Application Priority Data

May 8, 1979 [SE] Sweden ............................ 7904028

[51] Int. Cl.$^3$ .............................................. A61K 47/00
[52] U.S. Cl. .................................................... 514/779
[58] Field of Search ........................ 424/358, 362, 363

[56] References Cited

FOREIGN PATENT DOCUMENTS

| | | | |
|---|---|---|---|
| 75090 | 11/1952 | Denmark | 424/363 |
| 569520 | 2/1933 | Fed. Rep. of Germany | 424/363 |
| 932817 | 9/1955 | Fed. Rep. of Germany | 424/363 |
| 1367858 | 6/1964 | France | 424/362 |
| 46-35760 | 10/1971 | Japan | 424/361 |
| 26987 | of 1912 | United Kingdom | 424/362 |
| 322607 | 12/1929 | United Kingdom | 424/363 |
| 342947 | 2/1931 | United Kingdom | 424/363 |
| 1050967 | 12/1966 | United Kingdom | 424/362 |

OTHER PUBLICATIONS

Janistyn, Riechstoffe Seifen Kosmetika, 1950, pp. 404 to 406.

*Primary Examiner*—Dale R. Ore
*Attorney, Agent, or Firm*—Burns, Doane, Swecker & Mathis

[57] ABSTRACT

A layer can be formed on skin, mucous membrane or other tissue by first applying an ointment on the skin or mucous membrane, said ointment containing a water-soluble alginate and an aqueous dispersion of hydrophilic lipid crystals. A calcium salt is then applied on the surface of the ointment, which converts the alginate to insoluble calcium salt. Pharmaceutically active components may be included in the ointment.

7 Claims, No Drawings

PROTECTIVE LAYER ON SKIN, MUCOUS MEMBRANE OR OTHER BODY TISSUE

CROSS-REFERENCE TO RELATED APPLICATIONS

This application is a continuation application of application Ser. No. 147,741, filed May 8, 1980, now abandoned.

TECHNICAL FIELD

The invention relates to a protective layer on skin, mucous membrane, or other tissue in the human or animal body. More particularly, the invention relates to a method for producing such a protective layer, an ointment to be used in said method, and means for producing such a protective layer. The invention may be used for medical purposes, but it may also be used for purposes in which no medical effect is involved.

BACKGROUND ART

It is known that a protective layer, an "artificial skin" can be produced on skin and mucous membrane. Such a protective layer may be desirable in the case of burns, bed-sores or to cover an operation wound, for instance. A solution of a polymer-forming substance in a solvent may be sprayed on the skin, for instance, so that a plastic film is formed when the solvent evaporates. One drawback with this procedure is that the organic solvent causes stinging and probably damages the tissues.

DISCLOSURE OF INVENTION

The invention aims at achieving a protective layer, the components of which are propitious to the tissues and have no toxic or allergic effects. The method according to the invention is characterised in that an ointment containing a soluble salt of alginic acid and an aqueous dispersion of hydrophilic lipid crystals is applied on the surface, after which a calcium salt is applied on top of the ointment to convert the alginic acid salt to insoluble calcium salt.

The ointment of the invention is characterized in consisting of 70–90 percent by weight aqueous phase, 8–25 percent by weight hydrophilic lipid crystals dispersed in the aqueous phase, and 1–7 percent by weight water-soluble salt of alginic acid dissolved in the aqueous phase.

The means of the invention for producing the protective layer is characterized in comprising two components, viz. a first component in the form of an ointment containing a soluble salt of alginic acid and an aqueous dispersion of hydrophilic lipid crystals, said ointment being intended for application on said surface, and a second component containing a calcium salt, said second component being intended for application on top of said ointment on said surface, to convert the soluble alginic acid salt to insoluble calcium salt.

The sodium salt, which is a natural product often used as consistency controlling agent in foodstuffs and pharmacological preparations, is preferred as water-soluble alginic acid salt. It is known that the calcium salt of alginic acid (polymannuronic acid) is insoluble in water. It is also known that it is possible to form a film on the surface of an alginate solution by bringing the surface into contact with calcium ions. The film is formed by the calcium ions forming bridges between the carboxyl groups of adjacent chains. The film has a very high mechanical strength, which is believed to be because cross-linked blocks are formed in which each sugar unit along the linear polymer is tied together by calcium bridges to corresponding blocks in adjacent molecules. However, it is not possible to make direct use of this film formation of calcium alginate on skin, partly due to the wetting properties of the skin. It has now been found that by mixing the water-soluble alginic acid salt with a dispersion of hydrophilic lipid crystals a composition is obtained having such adhesion and wetting properties that it can be spread on the skin and mucous membrane to form a coherent layer of desired thickness. The layer will adhere even to skin exuding liquid and to mucous membrane. It is therefore suitable as an ointment for damaged skin where it will serve at the same time as a bandage. It can, therefore, also be used to stop bleeding.

The alginic acid salt, which is preferably the sodium salt, should have a low average molecular weight, to that a high percent of the alginate can be incorporated into the ointment without the viscosity becoming too high. A suitable range for the molecular weight is 15,000–90,000. An example of a suitable quality of alginate is that marketed by Alginate Industries Ltd., London, under the trade name Manucol. This alginate is of "food/pharmaceutical grade". The types known as LB, LD, LF and LH have been found to be particularly suitable. They have average molecular weights within the range 18,000–88,000 and viscosities of about 4, 9, 25 and 60 cps, respectively. For mixing with the lipid dispersion the alginate should be in the form of an aqueous solution with a concentration of 3–8, preferably about 5, percent by weight. The weight ratio of alginate solution to lipid dispersion should be 0.5–4, preferably 1–2.

The dispersion of hydrophilic lipid crystals is preferably a dispersion of monoglyceride crystals such as is described in British Pat. No. 1,174,672. This is an aqueous dispersion of hydrophilic crstals of at least one alpha-monoglyceride of a fatty acid having 12–18 carbon atoms in the carbon chain. The crystals are thin, leafshaped crystals having on their two main surfaces a substantially monomolecular layer in which the polar glycerol end groups face out towards the surface of the crystal. The crystal therefore acquires a hydrophilic character.

Such a dispersion of hydrophilic lipid crystals can be produced by mixing at least one alpha-monoglyceride with water in such a quantity that the water content of the mixture is 50–90 percent by weight, and heating the mixture to a temperature above the conversion temperature, which is considered as the lowest temperature at which lipid particles in contact with an excess of water absorb water and are converted to spherical particles with marked birefringence, known as liposomes. In order to make sure of conversion taking place, it is preferred to heat to a temperature 5°–15° C. above conversion temperature. The temperature is then maintained until equilibrium has been achieved, and the mixture is then cooled while stirring, at a rate of 0.5°–5° C. per minute until crystallization occurs and the desired hydrophilic crystals are formed. Cooling is then continued to room temperature, stirring all the time.

The conversion temperature for alpha-monolaurin is about 45° C., for alpha-monomyristin about 50° C., for alpha-monopalmitin about 55° C., and for alpha-monostearin about 60° C.

Compounds other than monoglycerides of fatty acids can form hydrophilic, dispersed lipid crystals. One group of such compounds comprises monoethers of glycerol and a saturated fatty alcohol having 12-18, preferably 16-18, carbon atoms in the carbon chain, for example the monoglycerol either of hexadecyl alcohol. Another group of such compounds comprises alkali salts of phosphoric acid esters of a saturated fatty alcohol having 12-18, preferably 16-18, carbon atoms in the carbon chain, for example the sodium salt of hexadecyl hydrogen phosphate. These compounds, which in themselves are of hydrophobic nature, can be converted to hydrophilic crystals by means of the procedure described in British Pat. No. 1,171,672 mentioned above. The conditions relating to heating, cooling rate and water content which apply to the monoglyerides of fatty acids in said patent apply also to the other compounds referred to above.

The alginate solution and the lipid dispersion can be mixed by simply stirring at room temperature until an ointment is obtained which appears to be homogeneous. Glycerol or propylene glycol which dissolves in the water phase may be mixed into the ointment, resulting in the alginate film formed upon reaction with the calcium salt becoming more elastic. A suitable percentage of glycerol or propylene glycol is 5-10 percent by weight calculated on the water phase.

Pharmaceutically active substances may be mixed into the ointment, for instance antimicrobially active substances. These preparations of medicinal type are manufactured from sterile components and under sterile conditions.

The calcium salt should be applied to the ointment in the form of a relatively concentrated water solution, suitably having a concentration of 10-30, preferably about 20 percent by weight. We prefer to use calcium chloride or calcium acetate, and of these the acetate is preferred since it gives a higher pH value than the chloride.

Instead of dissolving the calcium salt in pure water it may be dissolved in an ointment consisting of the above water dispersion of hydrophilic lipid crystals. The percentage of calcium salt should also in this case be 10-30, preferably about 20 percent by weight, calculated on the amount of water in the ointment.

To produce the protective layer according to the invention, the ointment containing the alginate is first spread on the skin or mucous membrane in a layer of the desired thickness. Onto this is then sprayed the aqueous solution of the calcium salt, or a layer of the calcium-containing lipid ointment is applied. By varying the quantity of calcium salt it is possible to cross-link either the entire quantity of alginate or only the alginate located in a surface layer of the ointment applied. An "invisible glove" may be applied on the hands, for instance, by applying a thin layer of alginate-containing ointment and spraying onto this so much calcium solution that the entire quantity of alginate is cross-linked in insoluble form. In the case of a burn, for instance, a thick layer of alginate-containing ointment (the layer may be a centimeter thick in the middle) may be applied on the damaged skin, and only so much calcium solution be sprayed onto this that the alginate in a surface layer one millimeter thick is converted to insoluble form. It is thus possible to very the permeability to water of the finished protective layer by varying both the total thickness of the protective layer and the thickness of the layer containing precipitated insoluble alginate. A thick layer of ointment with a firm film on the surface has many advantages even when pharmaceutically active components are included in the ointment, such as steroides. One of the advantages is increased penetration of the active component into the skin by what is known as occlusion effect.

The film obtained according to the invention, which contains insoluble, cross-linked alginate, has surprisingly skinlike qualities and unexpectedly good strength. It seems as if the lipid crystals and the calcium alginate reinforce each other so that the strength of the film is greater than can be expected, considering the properties of the components.

BEST MODE OF CARRYING OUT THE INVENTION, WITH REFERENCE TO EXAMPLES:

Example 1

A: 35 parts by weight of a mixture of alpha-monolaurin and alpha-monomyristin in the ratio of 70:30 were mixed with 65 parts by weight water. The mixture was heated to 60° C., kept at that temperature for 10 minutes and then allowed to cool to room temperature at a cooling rate of 1° C. per minute, being stirred during the cooling process. While cautiously stirring, 100 parts by weight of a water solution containing 5 percent by weight sodium alginate Manucol LF was mixed into the lipid dispersion obtained.

B: A water solution was prepared containing 20 percent by weight calcium acetate.

C: The ointment according to A was spread on skin and the aqueous solution according to B was sprayed onto the ointment. Spraying was continued until the surface of the ointment looked moist. The quantity of calcium acetate was then sufficient to precipitate the entire quantity of alginate in the layer of ointment in insoluble form.

Example 2

A lipid dispersion was produced by mixing

A: 30 parts by weight alpha-monomyristin with 10 parts by weight glycerol and 60 parts by weight water, heating the mixture to 60° C. and then allowing it to cool to room temperature while being stirred, at a cooling rate of 1° C. per minute. 100 parts by weight of a water solution containing 5 percent by weight sodium alginate Manucol LF was then mixed, stirred cautiously, into the lipid dispersion.

B: To a part of the lipid dispersion obtained according to A (i.e. before the addition of alginate) was added 6 percent by weight calcium chloride, i.e. 10 percent of the water content of the dispersion. The mixture was stirred until the calcium chloride had dissolved in the water phase of the dispersion.

C: The ointment according to A was spread in a thin layer on skin. A thin layer of the dispersion according to B was then spread over the first layer. The calcium ions in this layer reacted with the alginate in the layer beneath to form insoluble calcium alginate.

Example 3

A: A dispersion of hydrophilic lipid crystals was produced as described in Example 1. This dispersion was then mixed, stirring carefully, with an equal part by weight of an aqueous solution containing 3 percent by weight sodium alginate Manucol LF, and also with 0.1 percent by weight hydrocortisone.

B: A water solution was prepared containing 20 percent by weight calcium acetate.

C: The ointment according to A was smoothed onto skin with exzema. The solution according to B was then sprayed onto the ointment until the surface of the ointment looked moist.

Example 4

A: 25 parts by weight alpha-monomyristin and 10 parts by weight alpha-monolaurin were mixed with 65 parts by weight water. The mixture was heated to 60° C., kept at this temperature for 10 minutes and then allowed to cool, while being stirred, to room temperature at a cooling rate of 4° per minute. 10 percent by weight of a 20 percent hydrogen peroxide solution was then mixed into the dispersion. One part by weight of the ointment thus obtained was then mixed with two parts by weight of a water solution containing 8 percent by weight sodium alginate Manucol LD.

B: A water solution was prepared containing 20 percent by weight calcium acetate.

C: The ointment according to A is suitable for burned skin and bed-sores. The ointment is first applied to the wounded skin. The solution according to B is then sprayed onto the ointment. If the wounded skin exudes liquid, it is preferred first to apply a liquid absorbing powder, such a Debrisan (registered trade mark), to the skin. Now the ointment according to A is applied on top of the liquid absorbing powder, preferably by being sprayed onto the powder. Finally, the solution according to B is sprayed onto the ointment from two to four times.

Example 5

A: 30 parts by weight batyl alcohol (monoether of glycerol and hexadecyl alcohol) were mixed with 70 parts by weight water. The mixture was heated to 60° C., kept at this temperature for 5 minutes and allowed to cool, while being stirred, to room temperature at a cooling rate of 4° C. per minute. Clioquinol was then mixed into the lipid crystal dispersion in a quantity of 2% of the total weight of the dispersion to a homogeneous mixture. One part by weight of the ointment thus obtained was mixed with one part by weight of a water solution of a 6 percent by weight sodium alginate Manucol LD.

B: A water solution was prepared containing 20 percent by weight calcium acetate.

C: The ointment according to A was smeared out on oral mucous membrane. The soution to B was sprayed on until the surface of the ointment looked moist.

Example 6

A: A mixture of 25 g sodium monotetradecyl phosphate and 75 g of distilled water was heated under stirring to 70° C. The temperature was kept constant for about 30 minutes, and then the mixture was cooled about 20° C. per hour down to room temperature. The cooling was done under constant stirring, which was fast enough to keep the mixture homogeneous by visual examination. When the mixture had reached room temperature it consisted of a dispersion of hydrophilic lipid crystals in water. To this dispersion was added 100 g of an aqueous solution containing 4 percent by weight of sodium alginate Manucol LF.

B: An aqueous solution containing 15 percent by weight of calcium acetate was prepared.

C: The ointment A was spread on the skin and the solution B was sprayed above. After drying it formed an "invisible glove" acting as skin protection.

I claim:

1. A method of producing a protective layer on a surface selected from the group consisting of skin and mucous membrane, said method comprising providing an ointment which comprises 70-90 percent by weight of an aqueous phase, 1-7 percent by weight of a water soluble salt of alginic acid having an average molecular weight of from 15,000 to 90,000 and 8-25 percent by weight of hydrophilic lipid crystals dispersed in said aqueous phase, said hydrophilic lipid crystals being selected from the group consisting of an alpha monoglyceride of a saturated fatty acid having 12-18 carbon atoms in the carbon chain, a glycerol monoether of a saturated fatty alcohol having 12-18 carbon atoms in the carbon chain, and an alkali metal salt of a phosphate ester of a saturated fatty alcohol having 12-18 carbon atoms in the carbon chain, applying said ointment to said surface, and contacting said ointment on said surface with an aqueous solution of a water-soluble calcium salt, said solution containing a concentration of calcium salt sufficient to convert at least said water soluble salt in the upper portion of said ointment on said surface to an insoluble calcium salt of alginic acid.

2. The method of claim 1 wherein said hydrophilic lipid crystals consist of thin leaves having on their surface a substantially monomolecular layer in which polar end groups face outwardly toward the surface of the crystal to provide a hydrophilic characteristic.

3. The method of claim 1 wherein said ointment comprises 1 part by weight of an aqueous suspension containing 10-40 percent by weight of hydrophilic lipid crystals and 0.5-4 parts by weight of an aqueous solution containing 3-8 percent by weight of said alginic acid salt.

4. The method of claim 1 wherein said calcium salt comprises calcium acetate.

5. The method of claim 1 wherein the calcium salt is applied in the form of an aqueous solution comprising 10-30 percent of calcium salt.

6. An ointment comprising 70-90 percent by weight of an aqueous phase, 8-25 percent by weight of hydrophilic lipid crystals dispersed in said aqueous phase, said lipid crystals being selected from the group consisting of an alpha monoglyceride of a saturated fatty acid having 12-18 carbon atoms in the carbon chain, a glycerol monoether of a saturated fatty alcohol having 12-18 carbon atoms in the carbon chain, and an alkali metal salt of a phosphate ester of a saturated fatty alcohol having 12-18 carbon atoms in the carbon chain, and 1-7 percent by weight of a water-soluble salt of alginic acid dissolved in said aqueous phase, said salt having an average molecular weight of from 15,000 to 90,000.

7. A two component composition for producing a protective layer on a surface selected from the group consisting of skin and mucous membrane, a first component in the form of an ointment comprising 70-90 percent by weight of an aqueous phase, 1-7 percent by weight of a soluble salt of alginic acid having an average molecular weight of 15,000 to 90,000 and 8-25 percent by weight of hydrophilic lipid crystals dispersed in said aqueous phase, said hydrophilic lipid crystals being selected from the group consisting of an alpha monoglyceride of a saturated fatty acid having 12-18 carbon atoms in the carbon chain, a glycerol monoether of a saturated fatty alcohol having 12-18 carbon atoms in the carbon chain, and an alkali metal salt of a phosphate ester of a saturated fatty alcohol having 12-18 carbon atoms in the carbon chain, said ointment being intended for application on said surface, and a second component comprising an aqueous solution of a water-soluble calcium salt for use in converting said water soluble salt to an insoluble calcium salt of alginic acid, said second component being intended for application on top of said ointment after said ointment has been applied to said surface, the concentration of said water-soluble calcium salt being sufficient to convert at least said soluble alginic acid salt in the upper portion of the ointment on said surface to said insoluble calcium salt.

* * * * *